(12) United States Patent
Bäck et al.

(10) Patent No.: US 9,956,124 B2
(45) Date of Patent: May 1, 2018

(54) PANT-TYPE ABSORBENT ARTICLE COMPRISING AN ELASTIC LAMINATE

(71) Applicant: SCA Hygiene Products AB, Göteborg (SE)

(72) Inventors: Lucas Bäck, Göteborg (SE); Stina Lindlöf, Göteborg (SE); Lennart Nilsson, Skärhamn (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days. days.

(21) Appl. No.: 15/515,455

(22) PCT Filed: Oct. 29, 2014

(86) PCT No.: PCT/SE2014/051275
§ 371 (c)(1),
(2) Date: Mar. 29, 2017

(87) PCT Pub. No.: WO2016/068764
PCT Pub. Date: May 6, 2016

(65) Prior Publication Data
US 2017/0216105 A1    Aug. 3, 2017

(51) Int. Cl.
*A61F 13/15*    (2006.01)
*A61F 13/20*    (2006.01)
(Continued)

(52) U.S. Cl.
CPC .... *A61F 13/4963* (2013.01); *A61F 13/49011* (2013.01); *A61F 13/49017* (2013.01);
(Continued)

(58) Field of Classification Search
CPC .......... A61F 13/49017; A61F 13/49406; A61F 13/496; A61F 13/51464
See application file for complete search history.

(56) References Cited

U.S. PATENT DOCUMENTS 5,496,298 A * 3/1996 Kuepper ........... A61F 13/49015
604/358
5,807,368 A * 9/1998 Helmer ............. A61F 13/49015
604/373
(Continued)

FOREIGN PATENT DOCUMENTS

EP          0 320 991 A2    6/1981
WO       WO 00/19951 A1    4/2000
(Continued)

OTHER PUBLICATIONS

International Search Report (PCT/ISA/210) dated Jul. 21, 2015, by the Swedish Patent Office as the International Searching Authority for International Application No. PCT/SE2014/051275.
(Continued)

*Primary Examiner* — Michele M Kidwell
(74) *Attorney, Agent, or Firm* — Buchanan Ingersoll & Rooney PC

(57) ABSTRACT

A pant-type absorbent article includes a front and a back portion, longitudinally extending side seams and a connecting portion between the front and back portions. The connecting portion forms a crotch region and leg openings. Part of the front portion, back portion, and the connecting portion is made of an elastic laminate extending transversely across the front, back and connecting portions. Elongated leg elastic members extend along the leg openings in at least part of the connecting portion and terminate at a distance from the respective side seam thus leaving an area corresponding to a peripheral length of at least 50 mm along the respective leg opening where the leg elastic members are absent and wherein the connecting portion in the area where the leg elastic members are absent is made of the elastic laminate in at least 90% of the peripheral length.

20 Claims, 4 Drawing Sheets

(51) Int. Cl.
*A61F 13/496* (2006.01)
*A61F 13/49* (2006.01)
*A61F 13/494* (2006.01)

(52) U.S. Cl.
CPC ............... *A61F 13/49413* (2013.01); *A61F 2013/49092* (2013.01)

(56) References Cited

U.S. PATENT DOCUMENTS

| | | | |
|---|---|---|---|
| 7,806,884 B2 | 10/2010 | Hildeberg et al. | |
| 8,641,695 B2 | 2/2014 | Edwall et al. | |
| 2002/0177829 A1 | 11/2002 | Fell et al. | |
| 2003/0028166 A1 | 2/2003 | Price et al. | |
| 2005/0055005 A1* | 3/2005 | Cazzato | A61F 13/49011 604/385.27 |
| 2008/0000003 A1* | 1/2008 | Melander | A61F 13/4902 2/69 |
| 2009/0088713 A1* | 4/2009 | Norrby | A61F 13/515 604/365 |
| 2009/0275911 A1 | 11/2009 | Hornung et al. | |
| 2010/0324513 A1 | 12/2010 | Wennerbäck | |
| 2012/0016334 A1 | 1/2012 | Nakajima et al. | |

FOREIGN PATENT DOCUMENTS

| | | |
|---|---|---|
| WO | WO 01/85080 A1 | 11/2001 |
| WO | WO 02/069871 A1 | 9/2002 |
| WO | WO 03/047488 | 6/2003 |
| WO | WO 2005/122985 A1 | 12/2005 |
| WO | WO 2007/008128 A1 | 1/2007 |
| WO | WO 2007/133127 | 11/2007 |
| WO | WO 2008/060205 A1 | 5/2008 |
| WO | WO 2009/136822 A1 | 11/2009 |
| WO | WO 2010/113472 A1 | 10/2010 |
| WO | WO 2011/162652 A1 | 12/2011 |

OTHER PUBLICATIONS

Written Opinion (PCT/ISA/237) dated Jul. 21, 2015, by the Swedish Patent Office as the International Searching Authority for International Application No. PCT/SE2014/051275.

* cited by examiner

PANT-TYPE ABSORBENT ARTICLE COMPRISING AN ELASTIC LAMINATE

TECHNICAL FIELD

The present disclosure relates to a pant-type absorbent article such as a pant diaper, a sanitary pant or incontinence pant. The article comprises a chassis region comprising a front portion and a back portion joined to each other along longitudinally extending side seams and further comprises a connecting portion between the front and back portions. The connecting portion forms a crotch region and leg openings. The article comprises an absorbent core located at least in the connecting portion. At least part of the front portion, the back portion and the connecting portion is composed of an elastic laminate comprising first and second layers of fibrous material and an elastic film layer located there between. The elastic laminate extends transversely across the width of the front portion, the back portion and the connecting portion. Elongated leg elastic members extend along the leg openings in at least part of the connecting portion.

BACKGROUND

Pant-type absorbent articles include a pant-shaped chassis and an absorbent core component integrated with the chassis. They are intended to fit comfortably and snugly about the wearer. It is further desirable that the articles are capable of being pulled up and down over the hips of the wearer to allow the wearer or caregiver to easily put on and remove the article when it has been soiled.

Pant-type absorbent articles, in which portions of the chassis are composed of an elastic laminate comprising first and second layers of fibrous material and an elastic film layer located there between, are known through for example WO 2005/122985 and WO 2007/133127. Chassis composed of elastic laminates of this type are relatively smooth with less wrinkles as compared to laminates comprising elastic strands sandwiched between fibrous materials, as disclosed in for example US 2003/0028166 and US 2009/0275911.

In WO 2005/122985 and WO 2007/133127 elongated leg elastic members extend along the crotch portion and along the leg openings of the back portion all the way to the side seams joining the longitudinal side edges of the back and front portions. The front portion may also have leg elastics. The leg elastics provide for a tight fit around the leg opening area to reduce leakage.

Discretion is an important aspect for pant-type absorbent articles of this kind. Although elastic laminates comprising an elastic film sandwiched between fibrous layers are relatively smooth, the added leg elastics, usually in the back portion of the pant, may cause wrinkling which can be seen through the clothing.

SUMMARY

One object of the disclosure is to provide a pant-type absorbent article of the kind referred to above, which is discrete to wear and fits snugly in the leg opening area providing security against leakage. The pant-type absorbent article according to the disclosure comprises elongated leg elastic members terminating at a distance from the respective side seam thus leaving an area corresponding to a peripheral length p of at least 50 mm along the respective leg opening where the leg elastic members are absent and wherein the connecting portion in said area where the leg elastic members are absent is composed of said elastic laminate in at least 80% of said peripheral length p.

The elastic film may be absent in part of the connecting portion.

A web material that is non-elastic or at least less elastic than said elastic laminate may be arranged in the connecting portion of the article where the elastic film is absent.

Said non-elastic or less elastic web material may extend transversely across the width of the connecting portion between the first and second leg openings.

Said elongated leg elastic members may extend along at least 90% of the part of the leg openings which are located in said non-elastic or less elastic web material where the elastic film is absent.

Said elongated leg elastic members may extend along the entire part of the leg openings which are located in said non-elastic or less elastic web material where the elastic film is absent.

Said elongated leg elastic members may extend along the entire part of the leg openings which are located in said non-elastic or less elastic web material where the elastic film is absent and overlap the elastic laminate.

Said non-elastic or less elastic web material may be a separate web material which is joined to the elastic laminate along transverse seams.

Said non-elastic or less elastic web material may comprise at least one of said first and second fibrous layers comprised in said elastic laminate, wherein said first and/or second fibrous layer extend beyond the area covered by the elastic film, said elastic film having a transverse edge constituting a boundary between said elastic laminate and said non-elastic or less elastic web material.

Said leg elastic members may terminate in an area located not more than 20 mm, preferably not more than 15 mm, from the respective seam or the respective transverse edge of the elastic film at any side thereof.

Said peripheral length p along the respective leg opening where the leg elastic members are absent may be at least 75 mm, preferably at least 100 mm.

The connecting portion in said area where the leg elastic members are absent may be composed of said elastic laminate in at least 85%, preferably at least 90% of said peripheral length p.

The leg openings may exhibit defined points where the width of the connecting portion increases abruptly and wherein a narrow area of the connecting portion located between said points defines a crotch region of the connecting portion and the wider areas outside said crotch region of the connecting portion as seen in longitudinal direction form a front part of the connecting portion and a back part of the connecting portion facing said front portion and said back portion respectively.

Said leg elastic members may comprise first elastic members extending along longitudinal edges of said crotch region of the connecting portion and second elastic members extending along the leg openings of the front part and/or the back part of the connecting portion outside the area of the crotch region.

Said second elastic members may be arranged only in said back part of the connecting portion.

BRIEF DESCRIPTION OF THE DRAWINGS

Embodiments of the invention will below be described in greater detail with reference to the accompanying drawings.

EMBODIMENTS OF THE INVENTION

The invention will in the following be closer described with reference to some embodiments shown in the accompanying drawings.

Figure 1:
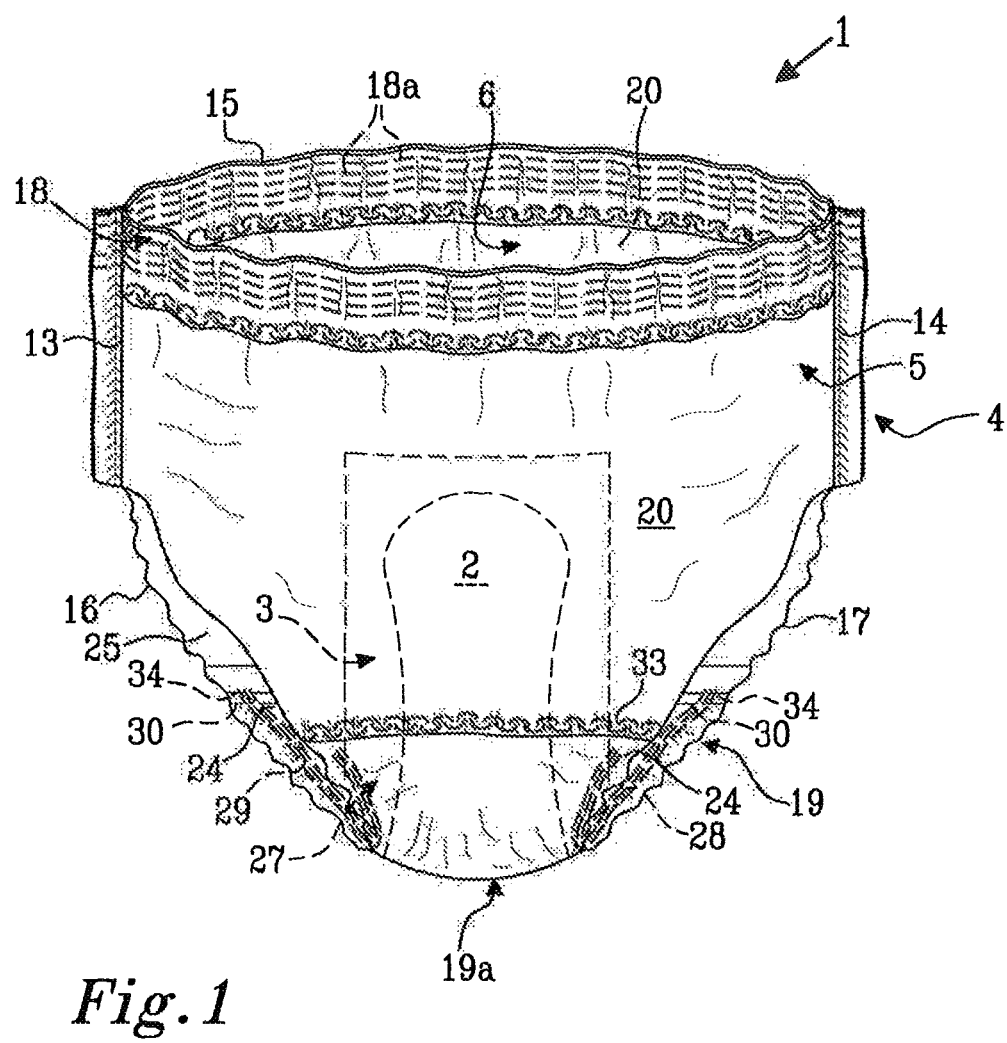
FIG. 1 is a perspective view of an embodiment of an absorbent pant article.
Figure 2:
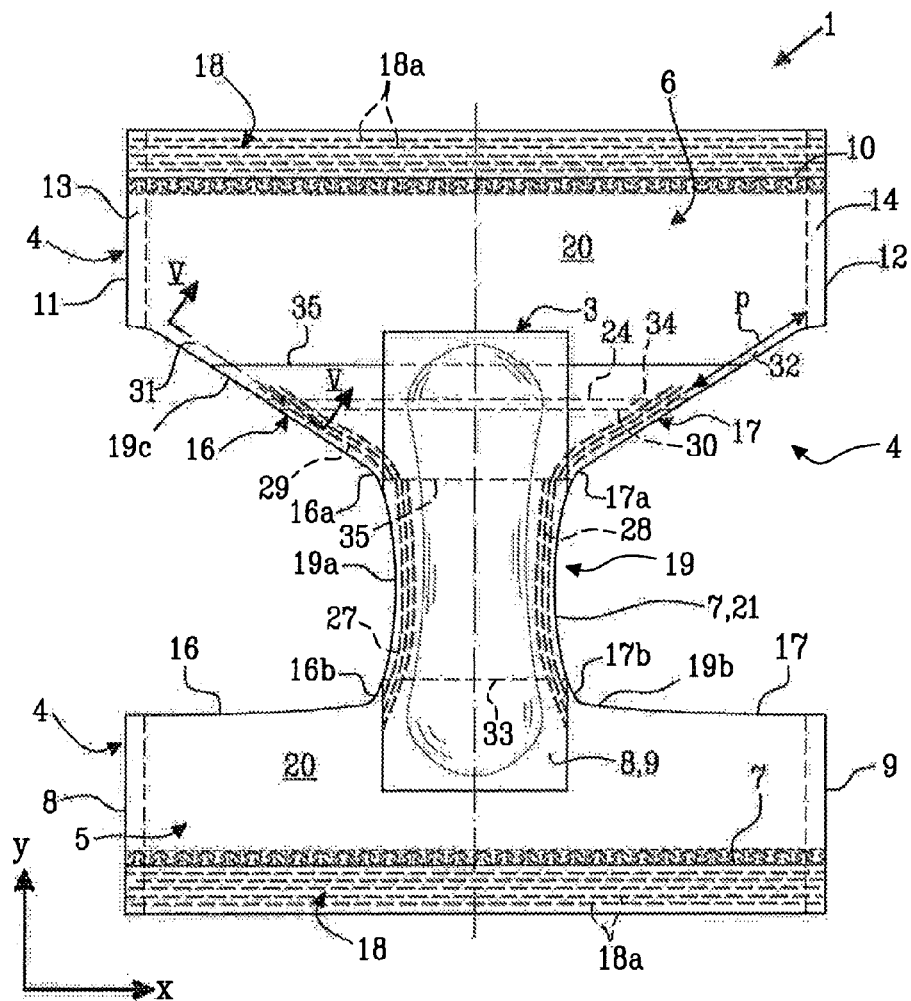
FIG. 2 is a simplified plan view of the absorbent pant article in its flat, non-contracted state.
Figure 3:
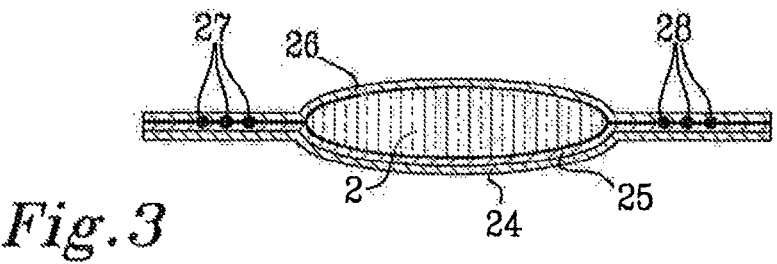
FIG. 3 is a cross section according to the line in FIG. 2.
Figure 4:
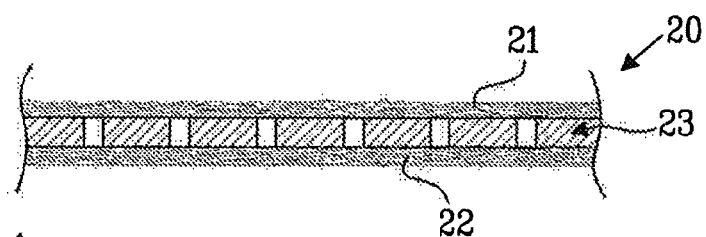
FIG. 4 is a cross section through an elastic laminate according to an embodiment of the invention.
Figure 5:
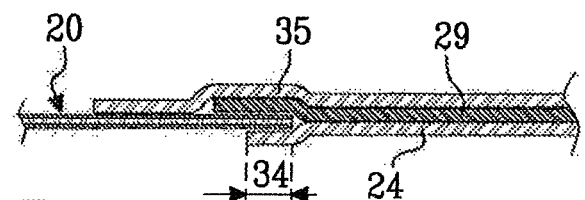
FIG. 5 is a schematic cross section according to the line V-V in FIG. 2.

The pant-type absorbent article 1 disclosed in FIGS. 1 and 2 is intended to enclose the lower part of the wearer's trunk like a pair of underwear. The disclosure mainly refers to disposable absorbent articles, which means articles that are not intended to be laundered or otherwise restored or reused as an absorbent article after use. The disclosure refers to pant-type absorbent articles such as a pant diapers, sanitary pants and incontinence pants and especially pant-type absorbent articles intended for adult wearers.

The pant-type absorbent article 1 comprises a core region 3 with an absorbent core 2. The article further comprises a chassis 4. The article has a longitudinal (y) and a transverse direction (x). The chassis 4 comprises a front portion 5 and a back portion 6. The front portion 5 has a front transverse edge 7 and first and second longitudinal side edges 8 and 9. The back portion 6 has a back transverse end edge 10 and first and second longitudinal side edges 11 and 12. The front and back portions 5 and 6 are joined to each other along their respective first and second longitudinal side edges by ultrasonic welds, glue strings or the like to form first and second side seams 13 and 14 and to define a waist-opening 15.

The chassis may further comprise an elastic waist band 18 comprising elongated elastic members 18a. The elastic waist band 18 is secured to the transverse end edges 7 and 10 of the front and back portions 5 and 6. The elastic waist band portions 18 are joined to each other along said side seams 13 and 14.

The article 1 further comprises a connecting portion 19 located between the front portion 5 and the back portion 6 in the longitudinal direction of the article. The connecting portion 19 defines a crotch region 19a and first and second leg openings 16 and 17. The boundary between the connecting portion 19 and the front and back portions 5 and 6 is along a transverse line extending between the lower edges of the side seams 13 and 14 adjacent the leg openings 16 and 17. The entire leg openings 16 and 17 are thus located in the connecting portion 19. The core region 3 is located in the connecting portion 19 and may extend into the front and/or back portions 5 and 6.

In the pant article shown in FIG. 2 the connecting portion 19 has defined points in the leg openings 16 and 17 where the width of the connecting portion 19 increases abruptly. These points are denoted 16a, 16b, 17a, 17b. In the pant article shown in FIG. 7 the leg openings 16 and 17 have a more or less continuous curvature with no such abrupt change of the radius of curvature.

A backsheet material 25 underlies the absorbent core 2 and adjacent areas immediately outside the absorbent core 2. The backsheet is preferably liquid-impervious. The area covered by the backsheet 25 is defined as the core region 3.

A liquid-pervious topsheet material 26 is arranged on the wearer-facing side of the absorbent core 2, so that the absorbent core 2 is enclosed between the backsheet material 25 and the topsheet material 26. The absorbent core 2, the backsheet 25 and the topsheet 26 form an absorbent assembly.

The preferably liquid-impervious materials used for the backsheet 25 may be a thin plastic film, e.g. a polyethylene or polypropylene film, a nonwoven material coated with a liquid impervious material, a hydrophobic nonwoven material which resists liquid penetration or a laminate comprising plastic films and nonwoven materials. The backsheet 25 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens.

The liquid-pervious materials used for the topsheet 26 may be a nonwoven material, e g spunbond, meltblown, carded, hydroentangled, wetlaid etc. Suitable nonwoven materials can be composed of manmade fibres, such as polyester, polyethylene, polypropylene, viscose etc. or natural fibers, such as woodpulp or cotton fibres, or from a mixture of natural and manmade fibres. Further examples of topsheet materials are porous foams, apertured plastic films etc.

The absorbent core 2 can be of any conventional kind. Examples of common absorbent materials used in absorbent cores are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core.

It is conventional in absorbent articles to have an absorbent core 2 comprising layers of different properties with respect to liquid receiving capacity, liquid distribution capacity and storage capacity. The thin absorbent bodies, which are common in for example baby diapers and incontinence articles, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core 2 may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

At least part of or the entire front and back portions 5 and 6 are composed of an elastic laminate material 20. By the term "elastic" is meant that the material is capable of being extended under a force and then is capable of contracting back to or towards its initial length once the force is removed. For the purpose of the present invention an "elastic" material should have an elasticity in at least one direction of at least 30% as measured by the Elasticity test specified herein. The elastic laminate 20 used in the pant-type absorbent article according to the invention should have elasticity in the x-direction of the article of at least 30%, preferably at least 50%, more preferably at least 70%, as measured by the Elasticity test specified herein.

Preferably the elastic laminate material 20 is also elastic in the y-direction of the article. However the elasticity in the y-direction is preferably lower than in the x-direction.

The term "non-elastic" refers to any material that does not fall within the definition of an "elastic" material given above.

The elastic laminate 20 may cover the entire article, including the core region 3 and the entire chassis region 4. However in a preferred embodiment a part of the connecting portion 19 of the article is free from the elastic laminate material 20. The part of the connecting portion 19 that is free from the elastic laminate 20 includes the narrow part which is referred to as the crotch region 19a. The waist band 18 may or may not be free from the elastic laminate material 20. The waist band may comprise a nonwoven material that is elasticized by elongated elastic members 18a, such as elastic threads, contractably affixed between material layers, such as nonwoven materials. Ultrasonic welds, glue strings or the like, join the elastic laminate 20 to the elastic waist band 18.

The elastic laminate 20 preferably extends continuously laterally across the width of the front portion 5 between the first and second side edges 8 and 9 as well as continuously laterally across the width of the back portion 6 between the first and second side edges 11, 12. The elastic laminate 20 also extends continuously laterally across the width of the connecting portion 19 between the leg openings 16 and 17 in those parts of the connecting portion 19 where the elastic laminate 20 is present.

The elastic laminate 20 is composed of first and second layers of fibrous material 21 and 22 and a an elastic film 23 located between said fibrous layers. The elastic laminate 20 may also comprise one or more additional fibrous layers laminated to one or both of the first and second fibrous layers. Such additional fibrous layers may be present only in parts of the elastic laminate 20. Thus the elastic laminate 20 need not be identical all over its area, but may comprise different layers in different areas.

It is advantageous that the outer fibrous layers are chosen so that they, in combination with the inner elastic film layer, give the material high resistance to puncture. They also provide a soft and cloth-like feel to the laminate. Examples of suitable materials are carded webs and spunbond materials. The basis weight of the fibrous material layers should be between 8 and 35 $g/m^2$, preferably between 10 and 25 $g/m^2$, more preferably between 12 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

At least one of the fibrous layers of the elastic laminate may be a creped nonwoven material. The creped nonwoven will increase the puncture resistance of the laminate puncture resistant and allow it to be subjected to the pulling and stretching forces that occur when putting on and taking off the pant article without breaking and tearing.

The middle layer is preferably an apertured elastic film 23 having a basis weight between 20 and 80 $g/m^2$, preferably between 20 and 60 $g/m^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

It is further preferred that the elastic laminate 10 has a breathability (Water Vapour Transmission Rate) according to ASTM E96-00 Procedure D of at least 1500 $g/m^2$ 24 h, preferably at least 3000 $g/m^2$ 24 h.

The open area of the elastic film layer is preferably at least 5%, more preferably at least 8%. The open area is measured by image analysis methods and is defined as the sum of the hole area divided by the total area of the film sample.

One method for manufacturing an elastic laminate is WO 03/047488, wherein one spunbond layer is applied to the film, said film being in a tacky state and will thus bond to the spunbond layer, while the other spunbond layer is adhesively laminated to the film layer, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

According to the modified method at least one, preferably both fibrous layers, which are bonded to the elastic film are not, in contrast to the method described in WO 03/047488, completely torn upon manufacture of a laminate according to the present invention. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably the fibrous layers, or at least one of the fibrous layers has an elongation at maximum load that is at least 10% higher than the elasticity of the laminate. This is described in more detail in WO 2005/122985.

In an alternative embodiment the laminate 20 is manufactured by feeding a first fibrous layer in the form of a nonwoven web into a bonding nip and extruding a molten elastic film-forming polymer through a die into the nip. The first fibrous layer and the elastic film form a first laminate. In a second lamination step the film side of the first laminate is coated or sprayed with adhesive and is subsequently passed through a second bonding nip together with a second fibrous layer to form the laminate 20. The laminate is subsequently activated by subjecting it to incremental stretching by passing it through intermeshing gears, IMG.

In a further embodiment the first layer of fibrous material and the elastic film layer form parts of a first elastic laminate that has been rendered elastic by incremental stretching and partial tearing of the first layer of fibrous material and in which the first elastic laminate has been bonded to the second layer of fibrous material while in a stretched state. The resulting laminate will then be elastically stretchable.

In a still further embodiment the first and second layers of fibrous material have been bonded to the elastic film layer while this is in a stretched state, so called stretch-bonding. The resulting laminate will be elastically stretchable.

The elastic laminate material 20 is preferably arranged as an outside coversheet material as well as inner coversheet material over at least part of the front portion 5, back portion 6 and connecting portion 19 of the chassis 4. The elastic laminate material may constitute the sole component of the chassis 4 in at least 20%, preferably at least 25%, more preferably at least 30% and most preferably at least 40% of the total surface area of the article, as seen in a flat state according to FIGS. 2 and 7.

No additional elasticized side panels joining the front and back portions 5 and 6 are needed when using the elastic laminate material 20 according to the invention.

The elastic laminate 20 and the backsheet 25 overlap in the outer parts of the core region 3, wherein the elastic laminate 20 is arranged on the garment facing side of the backsheet 25.

The absorbent assembly comprising the liquid impervious backsheet material 25, the liquid pervious topsheet material 26 and the absorbent core 2 enclosed therebetween, all of which components are described above, may be joined to the elastic laminate 20 of the front, back and/or connecting portions 5, 6 and 19 while this is held in a selectively stretched condition, so that gathers are present in the absorbent assembly at those points where it is joined to the front, back and/or connecting portions 5, 6 and 19.

As mentioned above the elastic laminate 20 may be absent in a substantial part of the connecting portion 19 of the article. A crotch panel material 24 may underlie at least part of the absorbent assembly on the garment-side thereof. The crotch panel material 24 may be of a non-elastic web material, although elastic materials may also be used. In case an elastic material is used as crotch panel material 24 it should be less elastic than the elastic laminate 20. Suitably, the crotch panel material is a nonwoven material. The crotch panel material 24 is joined to the elastic laminate 20 along seams 33 and 34.

Preferably the elastic laminate 20 is held in a stretched condition when joined to the non-elastic crotch panel material 24, wherein gathers are formed in the crotch panel material when the stretching force is released.

Figure 6:
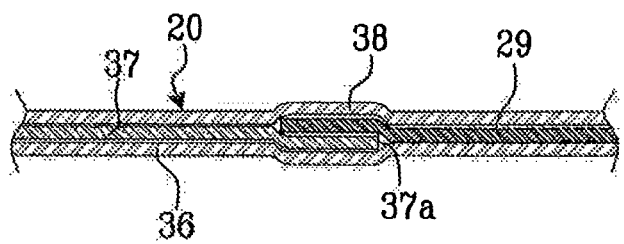
FIG. 6 is a schematic cross section similar to FIG. 5 but illustrating another embodiment.

In an alternative embodiment illustrated in FIG. 6 there is no separate crotch panel material 24 joined to the elastic laminate 20 along seams, but the elastic laminate 20 is defined by an elastic film 37 laminated to only part of inner and outer nonwoven layers 36 and 38, wherein the transverse edge 37a of the elastic film 37 forms the boundary between the elastic laminate and the non-elastic crotch panel material. This will be described more in detail below.

Elongated leg elastic members such as elastic threads extend along part of the leg openings 16 and 17 in the connecting portion 19. In the embodiment disclosed in FIG. 2 the leg opening elastic members are divided in first elastic members 27 and 28 extending along the respective longitudinal edges of the crotch region 19a and second elastic members 29 and 30 extending along the edges of part of the leg openings 16 and 17 outside the area of the crotch region 19a. The area of the connecting portion 19 outside the crotch region 19a and that faces the front portion 5 is defined as the front part 19b of the connecting portion 19 and the area of the connecting portion 19 outside the crotch region 19a and that faces the back portion 6 is defined as the back part 19c of the connecting portion 19.

The first elastic members 27 and 28, which extend along the narrow part of the connecting portion 19 referred to as crotch region 19a provide for a sealing effect in the crotch part preventing leakage of body fluid.

Figure 7:
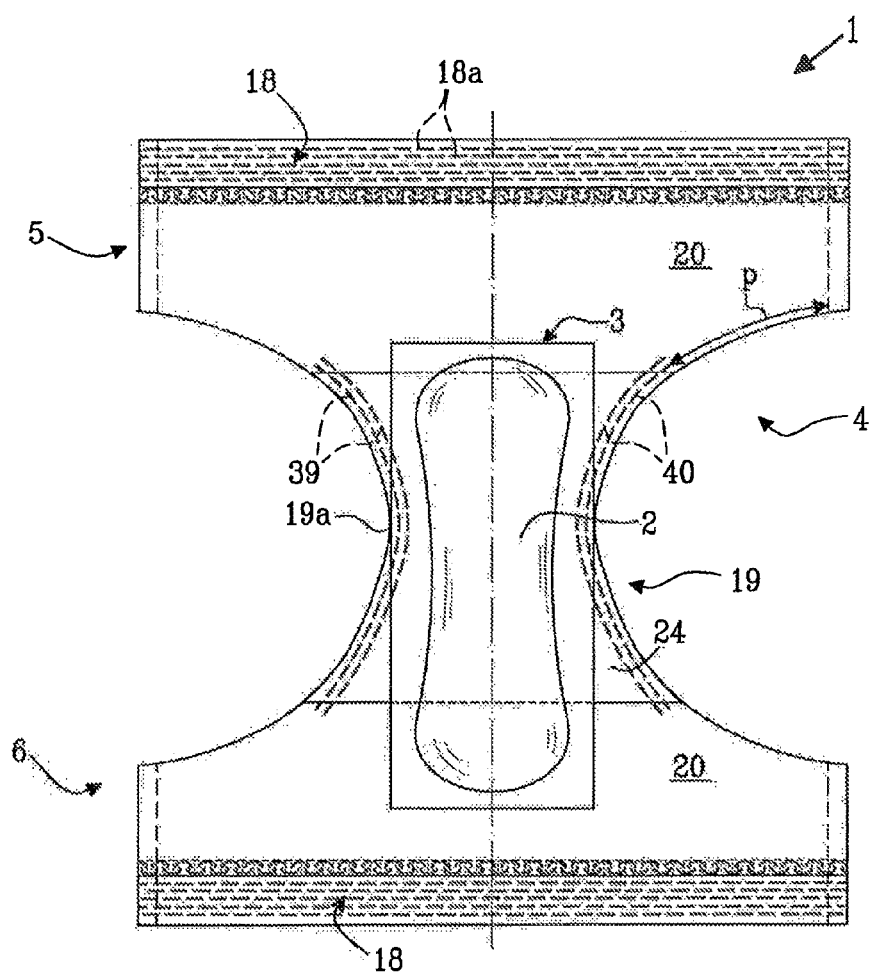
FIG. 7 is a plan view similar to FIG. 2 but showing a further embodiment of an absorbent pant article.

In the embodiment disclosed in FIG. 7 leg elastic members 39, 40 extend continuously along part of the leg openings 16 including the crotch region 19a.

In the embodiments shown in the drawings the elastic laminate material 20 covers more or less the entire front portion 5, the entire back portion 6 and part of the connecting portion 19, i.e. part of the leg opening area. In the embodiment disclosed in FIG. 2 the elastic laminate material 20 covers the entire front part 19b of the connecting portion 19 but only part of the back part 19c of the connecting portion 19. The part of the leg opening area in the connecting portion 19 covered by the elastic laminate 20 is elastic also in the absence of additional leg elastics.

In the embodiment shown in FIG. 2 the second elastic members 29 and 30 extend from an area adjacent the point 16a, 17a in the connecting portion 19 where the first elastic members 27 and 28 terminate and where the width of the article increases abruptly. The second elastic members 29 and 30 are only arranged in the back part 19c of the connecting portion 19 that is facing the back portion 6, while no second elastic members 29 and 30 are arranged in the front part 19b of the connecting portion 19.

The second elastic members 29 and 30 do not extend all the way to the side seams 13 and 14 but terminate in the leg openings 16 and 17 at a distance from the respective side seam 13 and 14 thus leaving an area 31 and 32 corresponding to a peripheral length p of at least 50 mm, preferably at least 75 mm and more preferably at least 100 mm along the respective leg opening 16 and 17 where the leg elastic members 29 and 30 are absent. The peripheral length p is measured along the periphery of the respective leg opening 16 and 17 and is measured to the inner edge of the respective side seam 13 and 14. When more than one elongated elastic member is present in the leg elastics (which normally is the case) the peripheral length (p) is measured from the elastic member where said length is shortest. The length p is measured in a flat, non-contracted state of the article as illustrated in FIG. 2. Said flat, non-contracted state of the article corresponds to the degree of stretching the elastic laminate has during the production process, when attaching non-elastic material components thereto.

The connecting portion 19 in the area adjacent the leg openings 16 and 17 where the leg elastic members 29 and 30 are absent is composed of the elastic laminate material 20 along at least 80%, preferably at least 85% and more preferably at least 90% of the peripheral length p.

As described above a crotch panel material 24 is arranged in the crotch region 19a of the connecting portion 19 and is joined to the elastic laminate 20 of the connecting portion 19. The crotch panel material 24 is preferably non-elastic. The leg elastic members 27-30 extend along at least part of the leg openings 16 and 17 in the connecting portion 19 defined by the crotch panel material 24. The leg elastic members 27-30 preferably extends along at least 90% of the part of the leg openings 16 and 17 which are located in said crotch panel material 24, wherein said length is measured along the periphery of the respective leg opening.

The leg elastic members 27-30 may extend a certain distance into the part of the leg openings 17 and 18 defined by the elastic laminate 20, or they may end in the boundary between the elastic laminate 20 and non-elastic crotch panel material 24, such as in a seam 34 joining the elastic laminate 20 to the crotch panel material 24. Preferably the leg elastic members 27-30 overlaps the elastic laminate 20 not more than 20 mm and more preferably not more than 15 mm.

A cover strip 35, preferably a nonwoven material, may be laminated on the wearer-facing side of the article covering the leg elastic members 29 and 30. The cover strip 35 preferably extends the entire width of the article. The cover strip 35 forms part of the elastic laminate 20 so that the part of the elastic laminate 20 to which the cover strip 35 is laminated maintains at least a substantial part of its elastic properties.

The leg elastics 29 and 30 retract the web material to which they are attached causing wrinkles, which can be seen through the clothing. The arrangement according to the invention of having leg elastics 29 and 30 that do not extend all the way to the side seams 13 and 14 results in smoother leg openings with less wrinkles and a more discrete article. Since at least a major part of the leg openings where the leg elastics are absent is composed of the elastic web material 20 there will be a certain sealing effect also in the area where the leg elastics are absent.

In an alternative embodiment of the invention illustrated in FIG. 6 there is no separate crotch panel material 24. Instead a base layer nonwoven 36 extends over the front, back and crotch portions 5, 6 and 19 and forms an outer coversheet material thereof. An elastic film 37 is laminated to the base layer nonwoven 36 in the front and back portions 5 and 6. A cover layer nonwoven 38 is laminated to the opposite side of the elastic film 37, and forms an inner coversheet of the article. The base layer nonwoven 36, the elastic film 37 and the cover layer nonwoven 38 forms an elastic laminate 20 according to the invention. The base layer nonwoven 36 and the cover layer nonwoven 38 are preferably per se non-elastic, wherein the article is elastic only in those parts where the elastic film 37 is present. The base layer nonwoven 36 and the cover layer nonwoven 38 form the crotch panel material in this embodiment.

The elastic film 37 extends preferably transversely across the width of the front portion 5 between the first and second side edges 8, 9, transversely across the width of the back portion 6 between the first and second side edges 11, 12 and transversely across part of the connecting portion 19 between the leg openings 16 and 17. The elastic film 37 has a transverse edge 37a at its end facing the crotch region 19a of the connecting portion 19.

Elongated leg elastic members 29 and 30 are attached between the base layer nonwoven 36 and the cover layer nonwoven 38 along part of the respective leg opening 16 and 17 at least in areas where the elastic film 37 is absent, in a corresponding manner as disclosed with respect to the embodiment described above. Preferably the leg elastic members 29 and 30 extend at least along 80%, preferably at least along 85% and more preferably along at least 90% of the part of leg openings 16 and 17 located in said area where the elastic film 37 is absent, wherein said length is measured as the peripheral length p along the respective leg opening. Preferably the leg elastic members 29 and 30 overlap the elastic film 37 not more than 20 mm and more preferably not more than 15 mm.

In the embodiment disclosed in FIG. 7 the leg openings 16 and 17 have a different curvature than in the embodiment disclosed in FIG. 2 and leg elastic members 39 and 40 extend continuously along part of the leg openings 16 and 17 including the crotch part 19b of the connecting portion 19. In other respects this embodiment is similar to the ones described above.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e., remaining, elongation of the relaxed material is measured.

A tensile tester, such as a Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

A non-elastic material is defined as a material having a permanent elongation after relaxation of more than 10% after having been subjected to an elongation of 30%.

The invention claimed is:
1. A pant absorbent article comprises:
a longitudinal and a transverse direction and a chassis comprising a front portion having a front transverse end edge and first and second longitudinal side edges, a back portion having a back transverse end edge and first and second longitudinal side edges,
wherein the front and back portions are joined to each other along their respective first and second longitudinal side edges to form side seams and define a waist opening,
said chassis further comprising a connecting portion between said front and rear portions forming a crotch region and first and second leg openings,
said article further comprising an absorbent core located at least in the connecting portion of the article, said absorbent core being arranged between a backsheet and a topsheet,
wherein at least part of said front portion, said back portion and said connecting portion are composed of an elastic laminate, said elastic laminate comprising first and second layers of fibrous material and an elastic film layer located there between,
said elastic laminate extends transversely across a width of the front portion from one of the side seams to another of the side seams, transversely across a width of the back portion from one of the side seams to another of the side seams and transversely across a width of the connecting portion between the first and second leg openings, and wherein elongated leg elastic members extend along the first and second leg openings in at least part of the connecting portion, wherein the elastic film layer extends without interruption transversely across the width of the front panel, and said elongated leg elastic members terminate at a distance from the respective side seam, thus leaving an area corresponding to a peripheral length of at least 50 mm along the respective leg opening where the leg elastic members are absent and wherein the connecting portion in said area where the leg elastic members are absent is composed of said elastic laminate in at least 80% of said peripheral length.

2. A pant absorbent article comprises:

a longitudinal and a transverse direction and a chassis comprising a front portion having a front transverse end edge and first and second longitudinal side edges, a back portion having a back transverse end edge and first and second longitudinal side edges, wherein the front and back portions are joined to each other along their respective first and second longitudinal side edges to form side seams and define a waist opening, said chassis further comprising a connecting portion between said front and rear portions forming a crotch region and first and second leg openings, said article further comprising an absorbent core located at least in the connecting portion of the article, said absorbent core being arranged between a backsheet and a topsheet, wherein at least part of said front portion, said back portion and said connecting portion are composed of an elastic laminate, said elastic laminate comprising first and second layers of fibrous material and an elastic film layer located there between, said elastic laminate extends transversely across a width of the front portion between the first and second longitudinal side edges, transversely across a width of the back portion between the first and second side edges and transversely across a width of the connecting portion between the first and second leg openings, and wherein elongated leg elastic members extend along the first and second leg openings in at least part of the connecting portion, and said elongated leg elastic members terminate at a distance from the respective side seam, thus leaving an area corresponding to a peripheral length of at least 50 mm along the respective leg opening where the leg elastic members are absent and wherein the connecting portion in said area where the leg elastic members are absent is composed of said elastic laminate in at least 80% of said peripheral length, wherein the elastic film is absent in part of the connecting portion.

3. The absorbent article as claimed in claim 2, wherein a web material that is non-elastic or at least less elastic than said elastic laminate is arranged in the connecting portion of the article where the elastic film is absent.

4. The absorbent article as claimed in claim 3, wherein said non-elastic or less elastic web material extends transversely across the width of the connecting portion between the first and second leg openings.

5. The absorbent article as claimed in claim 4, wherein said elongated leg elastic members extend along at least 90% of the part of the leg openings which are located in said non-elastic or less elastic web material where the elastic film is absent.

6. The absorbent article as claimed in claim 4, wherein said elongated leg elastic members extend along the entire part of the leg openings which are located in said non-elastic or less elastic web material where the elastic film is absent.

7. The absorbent article as claimed in claim 6, wherein said elongated leg elastic members extend along the entire part of the leg openings which are located in said non-elastic or less elastic web material where the elastic film is absent and overlap the elastic laminate.

8. The absorbent article as claimed in claim 3, wherein said non-elastic or less elastic web material is a separate web material which is joined to the elastic laminate along transverse seams.

9. The absorbent article as claimed in claim 3, wherein said non-elastic or less elastic web material comprises at least one of said first and second fibrous layers comprised in said elastic laminate, wherein said first and/or second fibrous layer extend beyond the area covered by the elastic film, said elastic film having a transverse edge constituting a boundary between said elastic laminate and said non-elastic or less elastic web material.

10. The absorbent article as claimed in claim 8, wherein said leg elastic members terminate in an area located not more than 20 mm from the respective seam or the respective transverse edge of the elastic film at any side thereof.

11. The absorbent article as claimed in claim 1, wherein said peripheral length along the respective leg opening where the leg elastic members are absent is at least 75 mm.

12. The absorbent article as claimed in claim 2, wherein the connecting portion in said area where the leg elastic members are absent is composed of said elastic laminate in at least 85% of said peripheral length.

13. The absorbent article as claimed in claim 1, wherein the leg openings exhibit defined points where the width of the connecting portion increases abruptly and wherein a narrow area of the connecting portion located between said points defines a crotch region of the connecting portion and wider areas outside said crotch region of the connecting portion as seen in longitudinal direction form a front part of the connecting portion and a back part of the connecting portion facing said front portion and said back portion, respectively.

14. The absorbent article as claimed in claim 13, wherein said leg elastic members comprise first elastic members extending along longitudinal edges of said crotch region of the connecting portion and second elastic members extending along the leg openings of the front part and/or the back part of the connecting portion outside the area of the crotch region.

15. The absorbent article as claimed in claim 14, wherein said second elastic members are only arranged in said back part of the connecting portion.

16. The absorbent article as claimed in claim 8, wherein said leg elastic members terminate in an area located not more than 15 mm from the respective seam or the respective transverse edge of the elastic film at any side thereof.

17. The absorbent article as claimed in claim 1, wherein said peripheral length along the respective leg opening where the leg elastic members are absent is at least 100 mm.

18. The absorbent article as claimed in claim 2, wherein the connecting portion in said area where the leg elastic members are absent is composed of said elastic laminate in at least 90% of said peripheral length.

19. The absorbent article as claimed in claim 1, wherein the pant absorbent article is a pant diaper, a sanitary pant, or an incontinence pant.

20. The absorbent article as claimed in claim 2, wherein the pant absorbent article is a pant diaper, a sanitary pant, or an incontinence pant.

* * * * *